(12) United States Patent
Nakao

(10) Patent No.: US 7,153,697 B2
(45) Date of Patent: Dec. 26, 2006

(54) FUNCTIONAL BEADS, METHOD FOR READING THE SAME AND BEAD-READING APPARATUS

(75) Inventor: Motonao Nakao, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 311 days.

(21) Appl. No.: 10/756,401

(22) Filed: Jan. 14, 2004

(65) Prior Publication Data

US 2004/0147031 A1 Jul. 29, 2004

(30) Foreign Application Priority Data

Jan. 23, 2003 (JP) ............... 2003-014379

(51) Int. Cl.
G01N 21/70 (2006.01)
G01N 21/62 (2006.01)
G01N 21/64 (2006.01)
G01N 21/66 (2006.01)

(52) U.S. Cl. ............... 436/172; 422/52; 422/82.08

(58) Field of Classification Search ............... 436/518, 436/523, 164, 172; 422/82.05, 82.07–82.08, 422/52; 977/774, 847
See application file for complete search history.

(56) References Cited

U.S. PATENT DOCUMENTS

| | | | |
|---|---|---|---|
| 6,023,540 A * | 2/2000 | Walt et al. ............... 385/12 | |
| 6,255,477 B1 | 7/2001 | Kleiber et al. | |
| 6,274,323 B1 * | 8/2001 | Bruchez et al. ............... 435/6 | |
| 6,309,701 B1 * | 10/2001 | Barbera-Guillem ............... 427/213.3 | |
| 6,472,224 B1 | 10/2002 | Wischerhoff et al. | |
| 6,500,622 B1 * | 12/2002 | Bruchez et al. ............... 435/6 | |
| 2002/0053532 A1 | 5/2002 | Quake et al. | |
| 2002/0081749 A1 * | 6/2002 | Kulmala et al. ............... 436/518 | |
| 2002/0164271 A1 | 11/2002 | Ho | |
| 2003/0008413 A1 | 1/2003 | Kim et al. | |
| 2003/0020022 A1 * | 1/2003 | Kuwabata et al. ............... 250/461.1 | |
| 2003/0165951 A1 * | 9/2003 | Bruchez et al. ............... 435/6 | |

FOREIGN PATENT DOCUMENTS

| | | |
|---|---|---|
| EP | 1249502 A2 | 9/2002 |
| WO | WO 02/099425 A2 | 6/2002 |
| WO | WO 03/003015 A2 | 6/2002 |

OTHER PUBLICATIONS

European Search Report dated Aug. 26, 2004.

* cited by examiner

Primary Examiner—Long V. Le
Assistant Examiner—Unsu Jung
(74) Attorney, Agent, or Firm—Reed Smith LLP; Stanley P. Fisher, Esq.; Juan Carlos A. Marquez, Esq.

(57) ABSTRACT

A method for reading beads comprising the steps of: introducing into a flow path functional beads having a coating layer on the surface thereof and having nanoparticles present in the coating layer; enabling the functional beads to emit light specific to the nanoparticles by applying a voltage to the functional beads in the flow path; and identifying the functional beads based on the emission. A bead-reading apparatus employing the method is also disclosed. Since conventional fluorescent beads are excited with a laser for reading fluorescence, light leakage occurs, so that the influence of noise cannot be ignored. The invention eliminates this drawback.

3 Claims, 4 Drawing Sheets (a)

(b)

(c)

FUNCTIONAL BEADS, METHOD FOR READING THE SAME AND BEAD-READING APPARATUS

BACKGROUND OF THE INVENTION

1. Technical Field

The present invention relates to beads that are easily identified and have various functions, a method for reading the beads, and a bead-reading apparatus.

2. Background Art

It is conventionally known that beads are used for nucleic acid detection. In addition, JP Patent Publication (Kokai) No. 6-300763 A (1994) discloses the use of fluorescent microbeads for immunoassay. Since beads with sizes on the order of microns are used as sites for a specific reaction between biopolymers, they are dyed in an organic solvent and then read or identified (discriminated) by a fluorescence microscope or a flow cytometer. However, bead identification is not easy, and it has been difficult to easily and accurately identify a large number of beads, particularly when the number of different kinds thereof ranges from the tens to the ten-thousands. Further, when a light source such as laser is used for excitation to read fluorescence, light leakage occurs, resulting in some background noises. Thus, accurate reading cannot be performed.

Particles with sizes on the nano-order such as semiconductor nanoparticles and metal nanoparticles are gaining attention as labeling means that can be used alternatively to organic coloring or fluorescence agents. The nanoparticle of the present invention may be a particle having a particle size of 10 nm or less, which is generally called a "quantum dot" or a "nanodot." The particle size thereof is preferably 1 to 5 nm. As kinds of materials used to form nanoparticles, known are metals such as gold, silver, palladium, and copper, semiconductors such as elemental semiconductors (Si, Ge, etc.) and compound semiconductors (GaAs, CdS, etc.), metal oxides such as titan oxide and tin oxide and chalcogenides.

Taking a semiconductor nanoparticle as an example, semiconductor nanoparticles of a grain size of 10 nm or less are located in the transition region between bulk semiconductor crystals and molecules. Their physicochemical properties are therefore different from those of both bulk semiconductor crystals and molecules. In this region, the energy band gap(=forbidden band) of a semiconductor nanoparticle increases as its grain size decreases, due to the appearance of quantum-size effects. In addition, the degeneracy of the energy band that is observed in bulk semiconductors is removed and the orbits are dispersed. As a result, the lower-end of the conduction band is shifted to the negative side and the upper-end of the valence band is shifted to the positive side.

Semiconductor nanoparticles can be easily prepared by dissolving equimolar amounts of precursors of Cd and X (X being S, Se or Te). This is also true for manufacturing CdSe, ZnS, ZnSe, HgS, HgSe, PbS, or PbSe, for example. However, the semiconductor nanoparticles obtained by the above method exhibit a wide grain-size distribution and therefore cannot provide the full advantages of the properties of semiconductor nanoparticles. Therefore, attempts have been made to attain a monodispersed distribution by using chemical techniques to precisely separate the semiconductor nanoparticles having a wide grain-size distribution immediately after preparation into individual grain sizes and extract only those semiconductor nanoparticles of a particular grain size. The attempts that have been reported so far include an electrophoresis separation method that utilizes variation in the surface charge of a nanoparticle depending on grain size, exclusion chromatography that takes advantage of differences in retention time due to differences in grain size, and a size-selective precipitation method utilizing differences in ability to disperse into an organic solvent due to differences in grain size. As a method that completely differs from the above methods, a size-selective optical etching method or the like has been reported, wherein the grain size of semiconductor nanoparticles is controlled by irradiating a solution of semiconductor nanoparticles with monochromatic light. Semiconductor nanoparticles obtained by these methods exhibit a spectrum with a relatively narrow wavelength-width peak.

As biologically specific reactions using beads with sizes on the micro-order as intermediates become more important from now on, there is a demand for developing a technology to easily identifying beads in order to make them usable. In particular, if large numbers of different kinds of beads, such as numbers ranging from the tens to the tens-thousands, are accurately and easily identified, the usability of beads is doubled. Additionally, when a light source such as laser is used for excitation and then fluorescence is read, light leakage occurs, so that accurate reading with the background light at zero level cannot be performed.

SUMMARY OF THE INVENTION

The present inventors have conducted intensive studies. As a result, they have solved the above problem using functional beads having a specific coating layer provided on the surface thereof.

Namely, a first aspect of the present invention is a functional bead comprising a coating layer on the surface thereof and having nanoparticles present in the coating layer.

The term "beads" used herein means micro particles each with diameters of 100 microns or less, for example, on the order of several microns, which are made of glass, plastic, ceramics, magnetic substances or the like. They are also called "microspheres." The beads of the present invention are not limited, and preferable examples of the beads include beads made of glass, silica gel, polystyrene, polypropylene, membrane, and magnetic substances.

Preferable examples of the coating layer include layers obtained by allowing alkoxides such as titan alkoxide and silicon alkoxide to be reacted through dehydration condensation. In addition, when the beads are made of plastic, the coating layer may be a layer obtained through polymerization of monomer.

The nanoparticle used in the present invention may be a particle having a particle diameter of 10 nm or less, which is generally called a "quantum dot" or a "nano dot." The size thereof is preferably 1 to 5 nm. However, the size is not necessarily limited since it differs depending upon the type of a material used for the formation of the nanoparticle or the function of interest. Further, the material constituting a nanoparticle is not particularly limited. Examples thereof include metals such as gold, silver, palladium, and copper; semiconductors such as elemental semiconductors (Si, Ge, etc.) and compound semiconductors (GaAs, CdS, etc.); and metal compounds such as metal oxides including titanium oxide and tin oxide, and chalcogenides, which are publicly known.

Semiconductor nanoparticles are particularly preferably used since they emit specific fluorescence depending upon the material or the size thereof. Preferable examples thereof include ZnO, ZnS, ZnSe, ZnTe, CdO, CdS, CdSe, CdTe, HgS, HgSe, HgTe, InP, InAs, GaN, GaP, GaAs, $TiO_2$, $WO_3$, PbS, and PbSe.

Although any kind of nanoparticle may be used alone, the use of 2 or more kinds thereof together is preferable since such use enables the identification of a large number of functional beads.

The functional beads of the present invention are prepared as follows. When glass beads, for example, are coated with metal alkoxide, nanoparticles such as semiconductor nanoparticles, which are functional particles, are simultaneously added. Thereafter, dehydration condensation of metal alkoxide is induced by heating. In this way, the functional glass beads having a coating layer with nanoparticles on the surface thereof can be produced.

In the present invention, a principle for identifying a large number of functional beads will be explained by referring to specific examples. First, 2 kinds of semiconductor nanoparticles (with particle diameters of 4.2 nm and 5.5 nm) having different fluorescent wavelengths are prepared, and they are bound to polystyrene beads (with particle diameters of 0.1μ to 100 μm, and particularly preferably of 1 μm to 10 μm). The material and the binding method of the beads used are not particularly limited. Here, 2 kinds of the semiconductor nanoparticles are dissolved in a solvent at various mixing ratios, and the solution is used as a fluorescence reagent for dyeing polystyrene beads.

FIG. 1 shows the relationship between the mixing ratios of the semiconductor nanoparticles and the intensity of emitted fluorescence. Here, 2 kinds of semiconductor nanoparticles having particle diameters of 4.2 nm and 5.5 nm, respectively, were mixed. The mixing ratios thereof are varied from 10:1 to 10:7, and they are used for dyeing polystyrene beads A to G, respectively. Results are shown, which are obtained by measuring the fluorescence intensity of beads A (4.2 nm semiconductor nanoparticles: 5.5 nm semiconductor nanoparticles=10:1) and beads B (10:2) with a flow cytometer. The beads A and B both have almost the same light intensity peaks at a wavelength of 570 nm corresponding to 4.2 nm semiconductor nanoparticles. However, the beads B have almost two times greater the relative light intensity between peaks at 625 nm corresponding to 5.5 nm semiconductor nanoparticles and at 570 nm corresponding to 4.2 nm semiconductor nanoparticles than the beads A. In this way, bead identification can be carried out using the relative intensity of light intensity peak at 625 nm to that at 570 nm as a signal.

The functional beads of the present invention have a nearly transparent surface coating layer. Thus, the nanoparticles may be buried in the surface coating layer, or may partially project from the surface of the coating layer.

A second aspect of the present invention is a method for reading beads. The method comprises the steps of: introducing into a flow path functional beads having a coating layer on the surface thereof and having nanoparticles present in the coating layer; enabling the nanoparticles to emit light with a wavelength specific to the nanoparticles by applying a voltage to the functional beads in the flow path; and identifying the functional beads based on the emission. This method makes use of the physical properties of the nanoparticles; that is, the fact that they emit light with a specific wavelength by applying a voltage to the functional beads of the first aspect of the present invention.

A third aspect of the present invention is a bead-reading apparatus comprising: a flow path through which functional beads having a coating layer on the surface thereof and having nanoparticles present in the coating layer pass; a pair of electrodes provided in the midst of the flow path, a power source to apply a voltage to the electrodes, and a light-receiving element for capturing light emitted from the functional beads, to which the voltage has been applied by the electrodes.

FIG. 2 illustrates a mechanism of light emission when the beads are in motion. In FIG. 2(a), beads 2 and 3 flow through the flow path 1 in the direction indicated by an arrow. In the midst of the flow path, a pair of electrodes 4 are provided. A predetermined voltage is applied to the electrodes 4 by a voltage generation apparatus 5. The electrodes are disposed to have a smaller space therebetween than the particle size of bead 2, such that the electrodes unfailingly come into contact with the surface of the bead. The widths of the flow path and the space between the electrodes are set depending on the particle size of the beads used. In general, the flow path preferably has a width 3 times or greater that of the bead particle size, and the space between the electrodes preferably has a size two-thirds or less that of the bead particle size. It is preferable that the electrodes 4 have a thin plate shape and are tilted and placed so that they are able to move in the forward direction of the bead-conveying path. In FIG. 2(b), when the bead 2 is brought into contact with both electrodes 4, the bead 2 has a current flow on its surface and the semiconductor nanoparticles on the bead surface is luminous glow (emit light). In FIG. 2(c), after a first bead passes through the electrodes, a next bead 3 is brought into contact with the electrodes 4, so that semiconductor nanoparticles on the bead surface glow in the same way as described above.

The fluorescence color of the light emitted from bead is determined with a photodiode 6 having RGB color filters as shown in FIG. 3, and the intensity of each color can be converted into a numerical figure. These numerical figures are processed with an image-processing apparatus 7. The photodiode 6 functions as a color sensor, thereby enabling the color of bead to be identified. In addition, a voltage, regardless of AC or DC, is applied and then light is emitted from beads under completely dark conditions, thereby making it possible to have the background light at zero level.

A fourth aspect of the present invention is a method for reading beads comprising the steps of: introducing into a flow path functional beads having a coating layer on the surface thereof and having nanoparticles present in the coating layer; irradiating the functional beads in the flow path with an electromagnetic wave to emit light with a wavelength specific to the nanoparticles; and identifying the functional beads with the emitted light. This method employs the physical properties of the nanoparticle, whereby the nanoparticle emits light with a wavelength specific thereto, by irradiating the functional beads of the above first aspect of the present invention with an electromagnetic wave. It is known, for example, that fluorescent lights having specific wavelengths are obtained by irradiating various semiconductor nanoparticles with an ultraviolet laser. In addition, reflected light from nanoparticles generated by irradiation of light from a white light emitting diode, a halogen lamp, or the like may be detected.

A fifth aspect of the present invention is a bead-reading apparatus comprising: a flow path through which functional beads having a coating layer on the surface thereof and having nanoparticles present in the coating layer pass; an electromagnetic wave source provided in the midst of the flow path; and a light-receiving element for capturing light emitted from the functional beads, which have been irradiated with the electromagnetic wave source.

FIG. 4 schematically illustrates an apparatus for reading the fluorescence intensity of nanoparticles on the surface of the beads. A bead 2 moving along a flow path 1 in the direction indicated by an arrow was irradiated with white light from a white LED 8 to excite semiconductor nanoparticles present on the bead surface, and then fluorescence from the semiconductor nanoparticles was introduced to a photodiode 6 with a optical fiber 9. In the same way as is described in FIG. 3, the photodiode 6 with RGB color filters can identify the color of light, and can convert the fluorescence intensity of each color into a numerical value. These numerical values are processed with an image-processing apparatus 7. The photodiode (color sensor) is arranged in a portion that is not exposed to ambient colors, since it measures fluorescence. Further, since this apparatus senses not only fluorescence from the bead but also forward or side scattered light (reflected light or scattered light), it can confirm whether the bead passes through the measuring portion of the flow path. At the same time the apparatus reflects the particle size of the bead, and therefore it is possible to measure the particle size thereof.

When a magnetic bead 10 is used, a magnetic belt 11 may be provided, as shown in FIG. 5, along each flow path 1 of the aforementioned bead-reading apparatus so that magnetic force enables the functional beads to pass through the flow path. The use of magnetic force as a means for moving the functional beads allows even fine beads to move smoothly.

A sixth aspect of the present invention is a functional bead comprising a coating layer on the surface thereof and having nanoparticles present in the coating layer, wherein a biopolymer is fixed on the surface of the functional bead. Herein, the term "biopolymer" means at least one type of protein, polyamino acid, DNA, RNA, synthetic polymer, or the like. The functional bead characterized by fixing such biopolymer on its surface is used as a biochip, such as a polymer chip for identifying an ionic polymer or a DNA chip. In particular, preferable examples thereof include a DNA chip as a probe having a double-stranded DNA made by complementarily binding a first DNA fixed on the surface of the functional bead to a second DNA.

A seventh aspect of the present invention is a method for reading functional beads comprising the steps of specifically causing the aforementioned biopolymers to react with other biopolymers in the presence of the functional beads of the sixth aspect of the present invention, and identifying the specific reaction with the functional beads. Herein, preferable examples of the specific reactions include hybridization reactions, nucleic acid amplification reactions, and antigen-antibody reactions.

In addition to the aforementioned, specific reactions can be caused using the functional beads of the present invention. For example, metal alkoxide may be used as a coating layer material and biopolymers of interest may be imprinted on the bead surface by the sol-gel method. This makes it possible to trap the target molecules on the bead surface.

An eighth aspect of the present invention is a flow cytometer characterized by having any one of the aforementioned bead-reading apparatuses. The incorporation of any one of the aforementioned bead-reading apparatus into the flow cytometer provides high level of discrimination without making the apparatus larger.

DETAILED DESCRIPTION OF THE DRAWINGS

EXAMPLES

Figure 1:
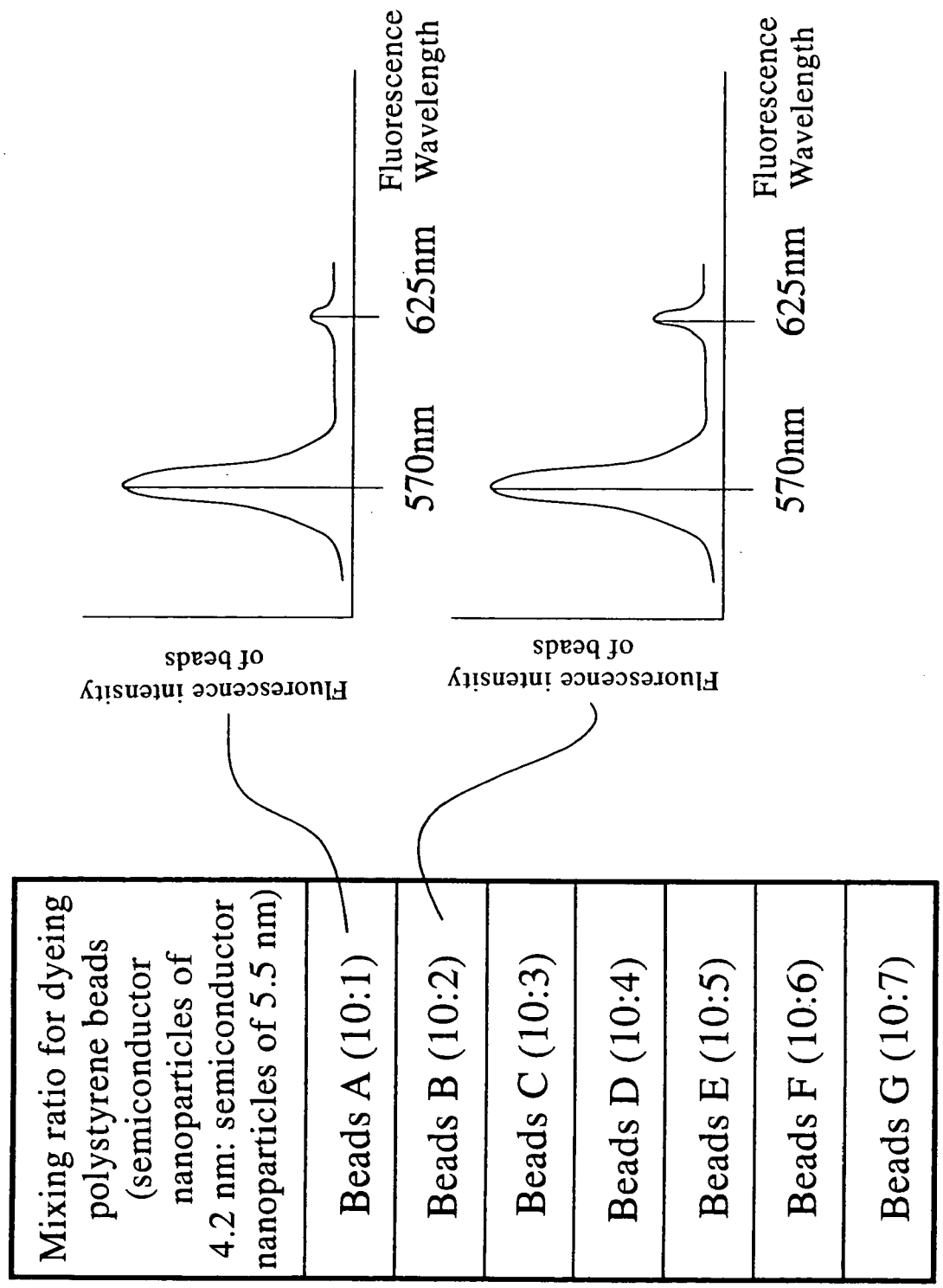
FIG. 1 illustrates a relationship between a mixing ratio of semiconductor nanoparticles and intensity of emitted fluorescence.
Figure 2:
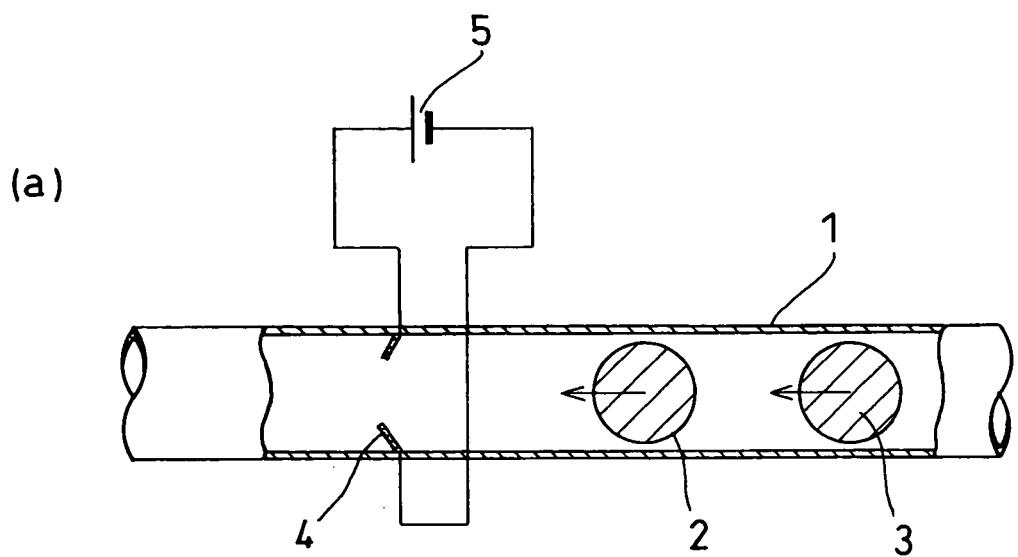
FIG. 2 illustrates a process wherein beads are in contact with a terminal portion when the beads move along a flow path.
Figure 2:
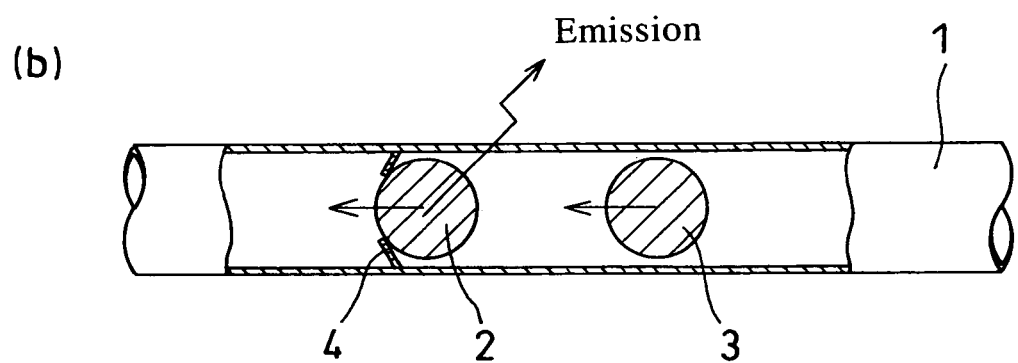
Figure 2:
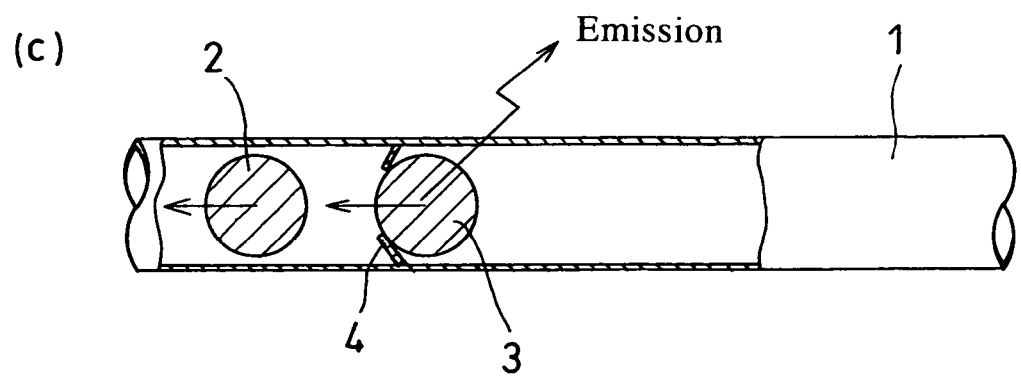
Figure 3:
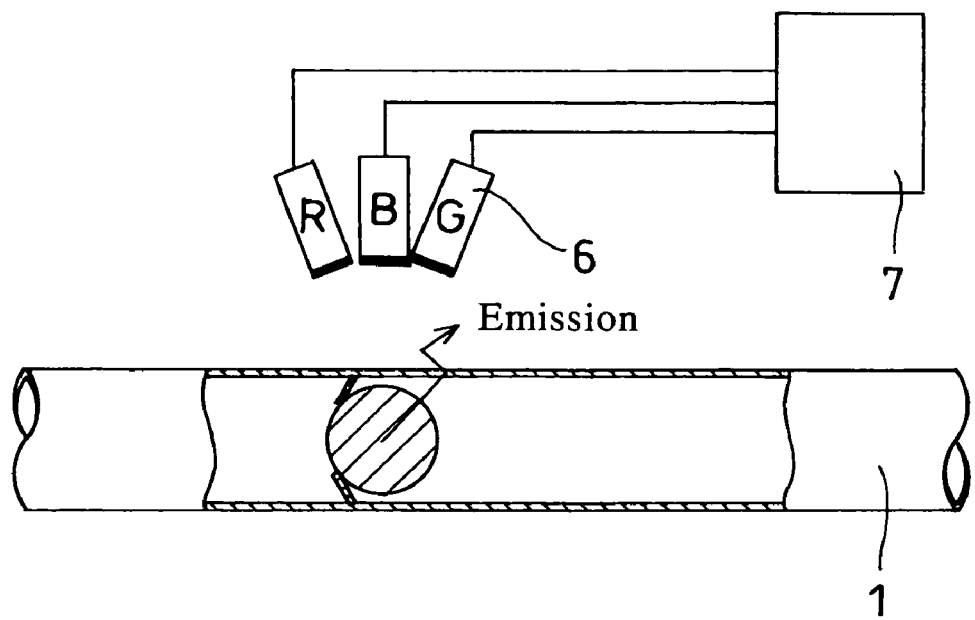
FIG. 3 is a schematic view of a reading apparatus which reads emissions from beads with a light-receiving element.
Figure 4:
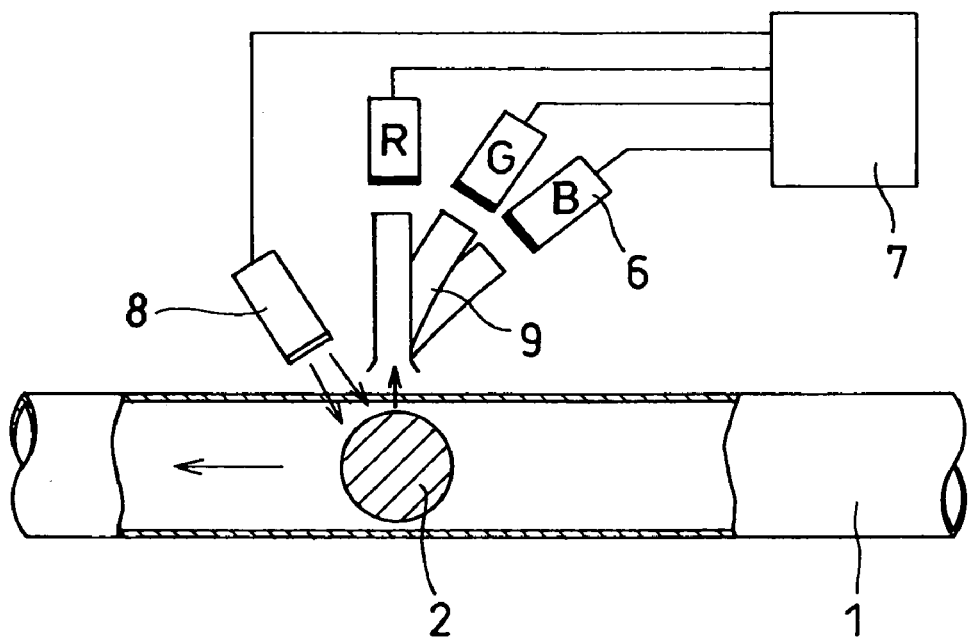
FIG. 4 is a schematic view of a reading apparatus which reads the fluorescence of beads.
Figure 5:
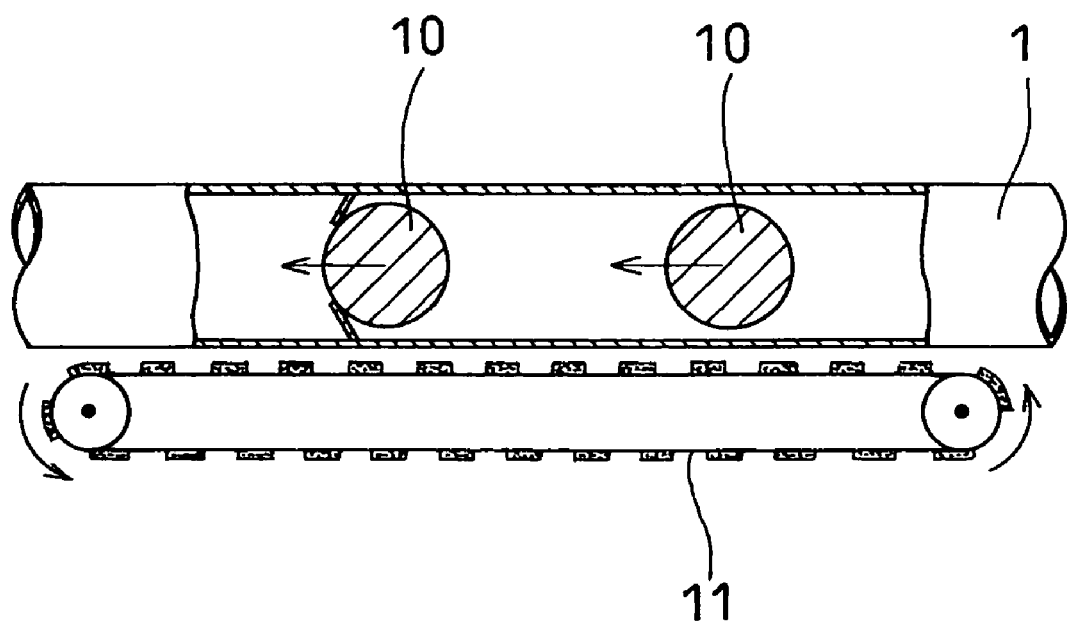
FIG. 5 illustrates beads moving along the flow path using magnetic force.

When the surface of a bead was coated with metal alkoxide, semiconductor nanoparticles were added as light-emitting material. As the 3 primary RGB colors of light, CdSe (wavelength: 700 nm) for red (R), GaP (wavelength: 550 nm) for green (G), and CdS (wavelength: 490 nm) for blue (B) were used. According to the color of interest, the amount of each type of semiconductor particle to be added was adjusted, and thereby beads with various colors could be produced.

According to the description in Nucleic Acid Research, 2000, Vol. 28, No 2, e5, DNA primers were attached onto glass beads using 3.1 μm CPG beads (Control Pole Glass (CPG Inc.)) and PCR was performed on the glass beads. However, in the case of conventional beads, even when different primers are bound to the beads, the primers cannot be classified with the beads. Therefore, there has been a demand for a method to identify beads for classification.

In this example, the surfaces of glass beads were coated with a reactive monomer $(C_2H_5O)_3TiOH$ produced through hydrolysis of metal alkoxide $Ti(OC_2H_5)_4$ by addition of $H_2O$. Simultaneously, semiconductor particles CdS as functional particles were admixed. The band gap of CdS as a semiconductor nanoparticle is 2.53 eV. Then, according to the following formula, $$E = h\nu = hc/\lambda = 1239.8/\lambda$$

wherein h represents Plank's constant ($6.626 \times 10^{-34}$ [J-sec]), C represents the speed of light, ν represents frequency, and λ represents wavelength. When a CdS semiconductor is excited, it emits light (blue) at 490 nm.

It is possible to control emission intensity by adjusting the amount of CdS semiconductor material to be admixed. Further, the color of light to be emitted can be changed by mixing with other types of semiconductor particles.

Based on such electroluminescence, beads can be identified, and thereby, for example, DNAs having different nucleotide sequences can be distinguished by attaching these DNAs to functional beads having different emission colors.

EFFECTS OF THE INVENTION

According to the present invention, beads can be easily identified, and also the reading sensitivity when identifying them can be improved. Additionally, apparatuses equipped with lasers such as a confocal laser microscope or a flow cytometer, are expensive and large in size. However, according to the present invention, emission generated by applying voltage improves the reading sensitivity and at the same time does not require equipment with a laser device, thereby making it possible to provide an inexpensive and compact apparatus.

What is claimed is:

1. A method for reading beads comprising the steps of:
introducing beads having a coating layer on a surface thereof and having nanoparticles present in the coating layer to a flow path wherein a pair of electrodes are disposed within the flow path so as to come into direct contact with the surface of each of the beads;

enabling the beads to emit light with a wavelength specific to the nanoparticles by applying a voltage to the beads in the flow path via the electrodes with which the beads have brought into contact, the voltage being applied to the electrodes; and identifying the beads based on the emission.

2. The method for reading beads according to claim 1, wherein the flow path has a width three times or greater a diameter of the bead.

3. The method for reading beads according to claim 1, wherein the space between the pair of electrodes is two-third or less a width of the bead.

* * * * *